(12) United States Patent
Terry et al.

(10) Patent No.: US 9,095,322 B2
(45) Date of Patent: Aug. 4, 2015

(54) SPECULUM WITH HINGED PORTION

(75) Inventors: Frederick M. Terry, Plymouth, MA (US); Dana Cote, Boxford, MA (US)

(73) Assignee: Beaver-Visitec International (US), Inc., Lake Forest, IL (US)

(*) Notice: Subject to any disclaimer, the term of this patent is extended or adjusted under 35 U.S.C. 154(b) by 6 days.

(21) Appl. No.: 13/238,582

(22) Filed: Sep. 21, 2011

(65) Prior Publication Data
US 2013/0072760 A1 Mar. 21, 2013

(51) Int. Cl.
*A61B 1/32* (2006.01)
*A61B 17/02* (2006.01)
*A61B 17/28* (2006.01)

(52) U.S. Cl.
CPC ......... *A61B 17/0231* (2013.01); *A61B 17/0206* (2013.01); *A61B 2017/2837* (2013.01)

(58) Field of Classification Search
CPC ............... A61B 17/02; A61B 17/0206; A61B 17/0218; A61B 17/0231; A61B 2017/2837; A61B 8/10; A61B 1/32; B25B 7/08; B25B 7/12; B25B 7/123; B25B 7/14; B25B 7/16; B25B 7/18
USPC ......... 600/201, 208, 210, 211, 214–217, 219, 600/220, 225, 226, 235–239, 242; 606/90, 606/191, 198; 81/318–340
See application file for complete search history.

(56) References Cited

U.S. PATENT DOCUMENTS

| | | | |
|---|---|---|---|
| 2,702,540 A | 2/1955 | Debeh | |
| 3,972,333 A | 8/1976 | Leveen | |
| 4,526,172 A | 7/1985 | Stephenson | |
| 5,002,561 A | 3/1991 | Fisher | |
| 5,341,798 A | 8/1994 | Grounauer | |
| 5,441,040 A | 8/1995 | Williams, Jr. | |
| 6,302,842 B1 * | 10/2001 | Auerbach et al. | 600/220 |
| 6,440,065 B1 | 8/2002 | Hered | |
| 6,544,169 B2 | 4/2003 | Putrino et al. | |
| 7,175,594 B2 | 2/2007 | Foulkes | |
| 7,625,391 B2 * | 12/2009 | Kebel et al. | 606/203 |
| D624,648 S | 9/2010 | Terry et al. | |
| D631,157 S | 1/2011 | Terry et al. | |

(Continued)

FOREIGN PATENT DOCUMENTS

| | | |
|---|---|---|
| DE | 102006021889 A1 | 11/2007 |
| FR | 712704 | 10/1931 |
| RU | 2020860 C1 | 10/1994 |

(Continued)

*Primary Examiner* — Michael T Schaper
*Assistant Examiner* — Tracy Kamikawa
(74) *Attorney, Agent, or Firm* — Hoffmann & Baron, LLP

(57) ABSTRACT

A speculum is provided herein which includes first and second arms, connected by a hinge, each having a channel formed thereon adapted to the shape of an eyelid. First and second elements are respectively located on the first and second arms configured to cooperatively retain the first and second arms in select rotational positions. A slot is defined in the second arm to partially separate first and second portions of the second arm with the first portion being displaceable away from the second portion. The second element is located on the first portion. Advantageously, with this arrangement, the first portion acts as a spring-loaded hinge which applies not only biasing force to the second element for retention, but also permits the second element to be separable from the first element. The subject invention provides a mechanical feature beyond the inherent memory of the material for operation of the speculum.

5 Claims, 6 Drawing Sheets

(56) References Cited

U.S. PATENT DOCUMENTS

| | | |
|---|---|---|
| D639,942 S | 6/2011 | Terry et al. |
| 2011/0098538 A1 | 4/2011 | Terry et al. |

FOREIGN PATENT DOCUMENTS

| | | |
|---|---|---|
| SU | 1736487 A1 | 5/1992 |
| WO | 9218055 A1 | 10/1992 |

* cited by examiner

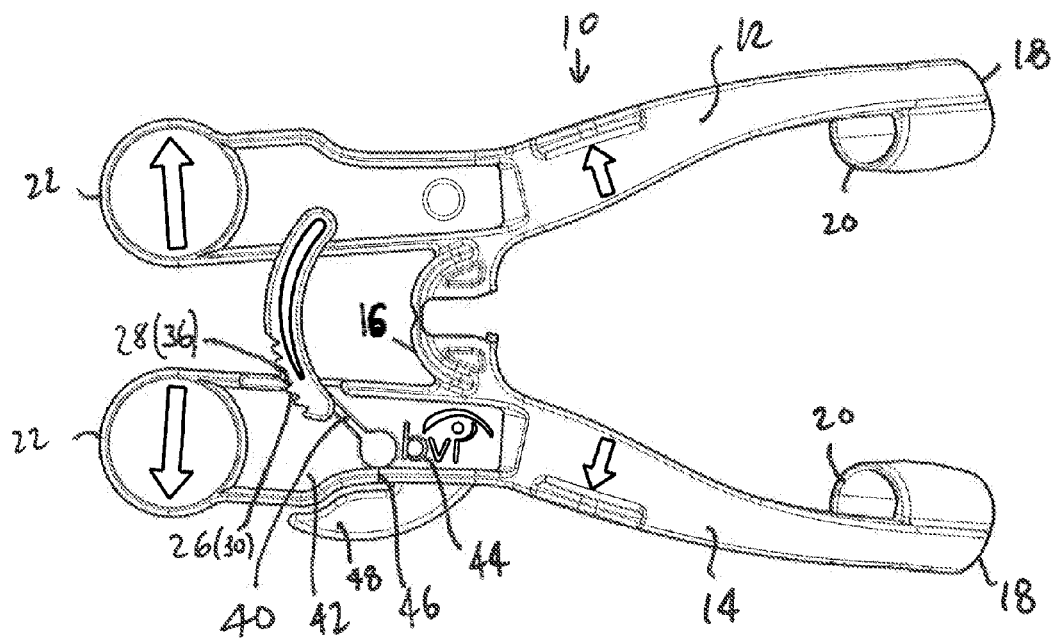
FIG. 6
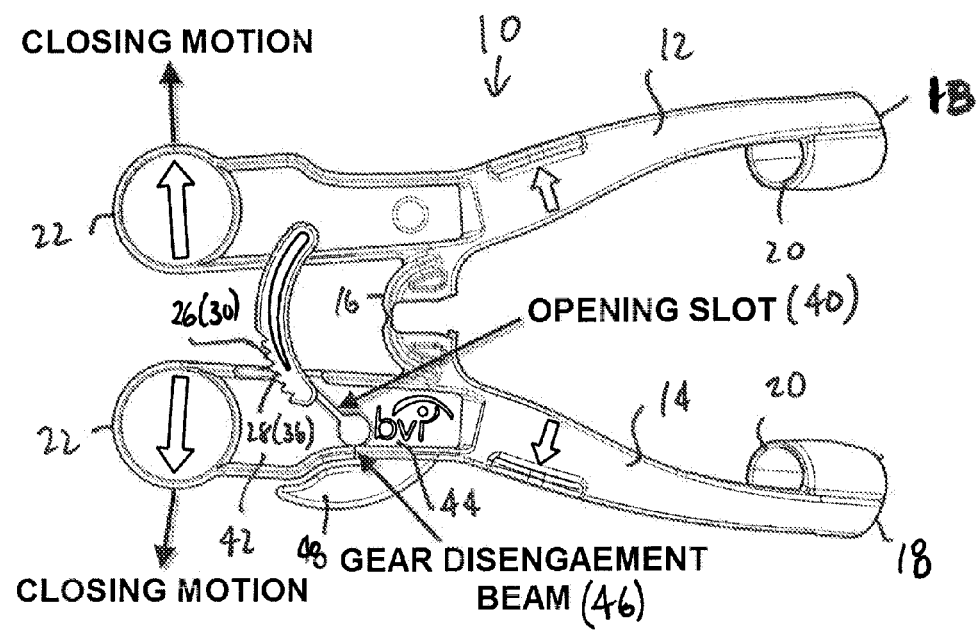

SPECULUM WITH HINGED PORTION

FIELD OF THE INVENTION

This invention relates to speculums for opening, and maintaining in an open position, eyelids, and, more particularly, to speculums having arrangements for being retained at specific opened positions.

DESCRIPTION OF THE PRIOR ART

Speculums are known in the prior art for opening, and maintaining in an open position, eyelids during ocular procedures or surgery. U.S. Published Patent Application No. 2011/0098538, which published on Apr. 28, 2011, to the inventors and assignee herein, discloses a unitarily formed speculum having an adjustable position retaining arrangement. With this speculum being formed of plastic material, the ability to permit adjustment of the position retaining arrangement and provide secure retention thereof at a desired portion is limited. Memory of the constituent material is relied upon to provide the retentive force; however, excessive deformation and other factors may undermine the material's inherent memory.

SUMMARY OF THE INVENTION

A speculum is provided herein which includes first and second arms, each having a channel formed thereon adapted to the shape of an eyelid. A hinge connects the first and second arms which permits the first and second arms to selectively rotate about an axis of rotation. The selective rotation causes the first and second channels to selectively move closer and farther apart. First and second elements are respectively located on the first and second arms, with the first and second elements being configured to cooperatively retain the first and second arms in select rotational positions with interfering interengagement between the first and second elements limiting rotation of the first and second arms. A slot is defined in the second arm to partially separate a first portion of the second arm from a second portion of the second arm with the first portion being displaceable away from the second portion. The second element is located on the first portion. Advantageously, with this arrangement, the first portion acts as a spring-loaded hinge which applies not only biasing force to the second element for retention, but also permits the second element to be separable from the first element. The subject invention provides a mechanical feature beyond the inherent memory of the material for operation of the speculum.

These and other features of the invention will be better understood through a study of the following detailed description and accompanying drawings.

BRIEF DESCRIPTION OF THE DRAWINGS

FIGS. 5 and 6 show the opening of a speculum formed in accordance with the subject invention;

FIGS. 7-9 show the closing of a speculum formed in accordance with the subject invention; and, FIG. 10 shows a maximum inward position of a speculum formed in accordance with the subject invention.

DETAILED DESCRIPTION OF THE INVENTION

Figure 1:
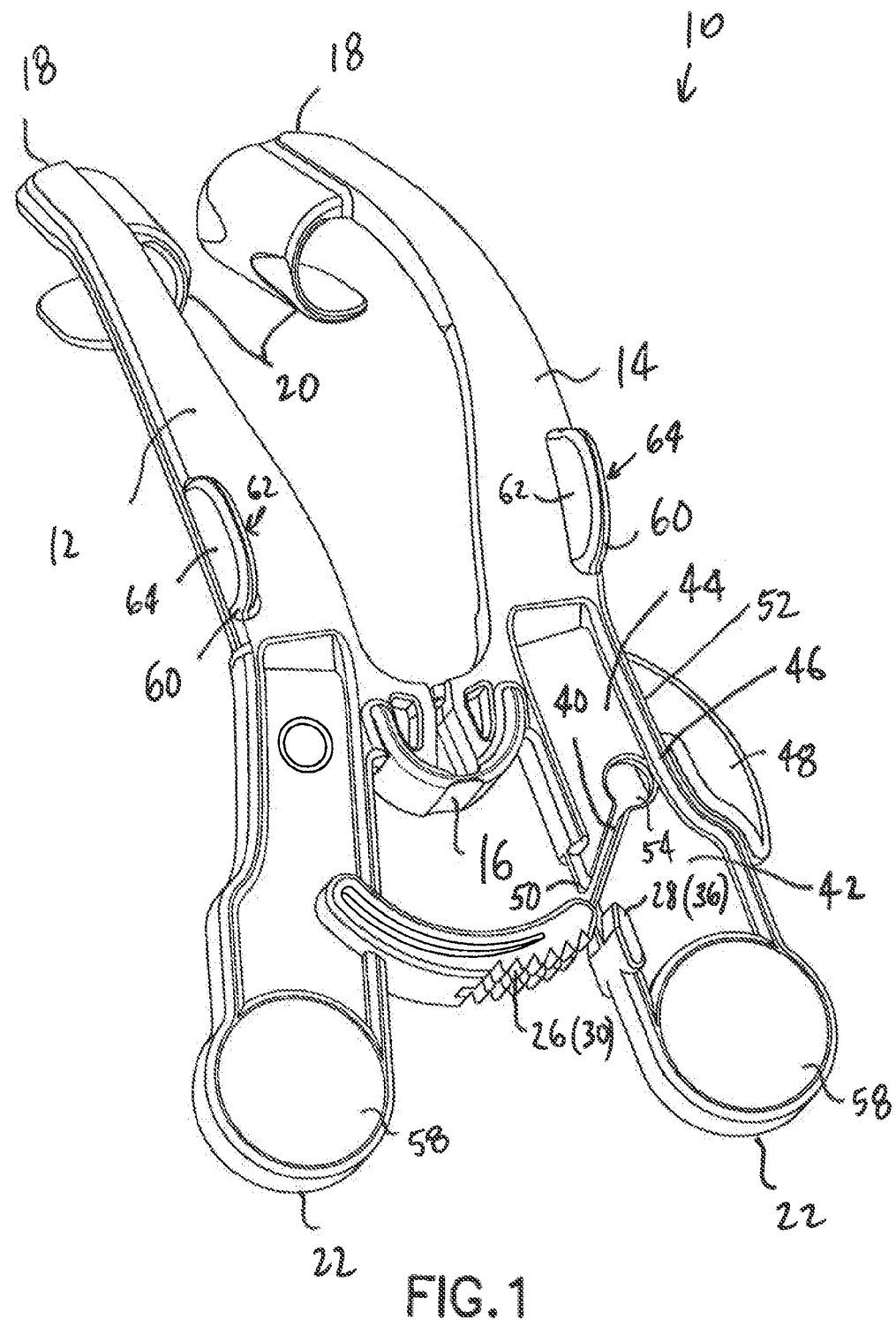
FIG. 1 is a perspective view of a speculum formed in accordance with the subject invention.

The subject invention relates to speculums which are useable for opening, and maintaining in an open position, eyelids during ocular procedures or surgery. Furthermore, the subject invention is directed to speculums formed from thermoplastic material, including, but not limited to, unitary, one-piece speculums. The subject invention provides improvements over such known designs. U.S. Published Patent Application No. 2011/0098538 A1, to the inventors and assignee herein, discloses various embodiments of such speculums. U.S. Published Patent Application No. 2011/0098538 A1 is incorporated by reference herein in its entirety.

With reference to the Figures, a speculum 10 is shown which includes first and second arms 12, 14 which are connected by a hinge 16. The first and second arms 12, 14 each include a distal end 18 having formed thereon a channel 20 adapted to the shape of an eyelid. Also, the first and second arms 12, 14 each include a proximal end 22, located opposite the distal end 18. In a preferred embodiment, as shown in the Figures, the hinge 16 is located at a mid-point of the first and second arms 12, 14 between the distal and proximal ends 18, 22. The first and second arms 12, 14 may be rotated about an axis of rotation, designated by reference numeral 24 (FIG. 4), to selectively cause the distal ends 18, and, hence, the channels 20, to come closer or further apart as need be. The axis of rotation 24 preferably coincides with the hinge 16 (FIG. 4), but, alternatively, may be spaced therefrom. Preferably, the speculum 10 is formed of thermoplastic material, such as high impact polystyrene (HIPS). Also, it is preferred that the speculum 10 be unitary. The speculum 10 may be formed by injection molding.

It is preferred that the speculum 10 be provided with a position retaining arrangement, whereby the first and second arms 12, 14 may be retained in a particular relative position. With reference to the Figures, complementary first and second elements 26, 28 are formed on the first and second arms 12, 14, respectively. Preferably, the first element 26 includes a series of teeth 30, each defining a peak 32. By way of non-limiting example, the teeth 30 may be saw-tooth shaped, but other shapes are possible. Recesses are defined between adjacent pairs of the teeth 30. The second element 28 preferably includes a pointer 36 formed to nest within the recesses 34 between the peaks 32 of adjacent pairs of the teeth 30. Two or more of the pointers 36 may be also arranged in series to engage the teeth 30.

Preferably, the teeth 30 are configured to by-pass the pointer 36 over a predetermined range of relative movement between the first and second arms 12, 14. The pointer 36 is formed to restrict movement of the teeth 30 relative thereto.

Figure 3:
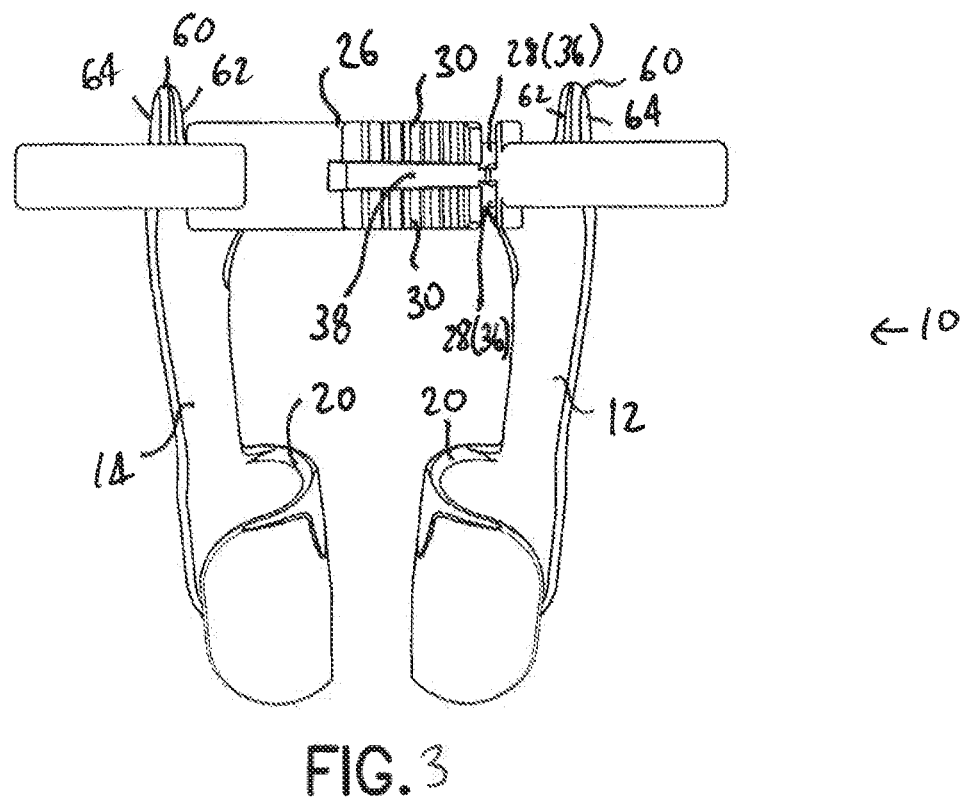

As shown in FIG. 3, in a preferred embodiment, a pair of the set of teeth 30 is provided with a channel 38 therebetween. The channel 38 permits the teeth 30 particularly the two sets of the teeth 30, to straddle a portion of the second arm 14, in providing stability during interengagement of the complementary elements 26, 28. In addition, a pair of the pointers 36 may be utilized.

Figure 4:
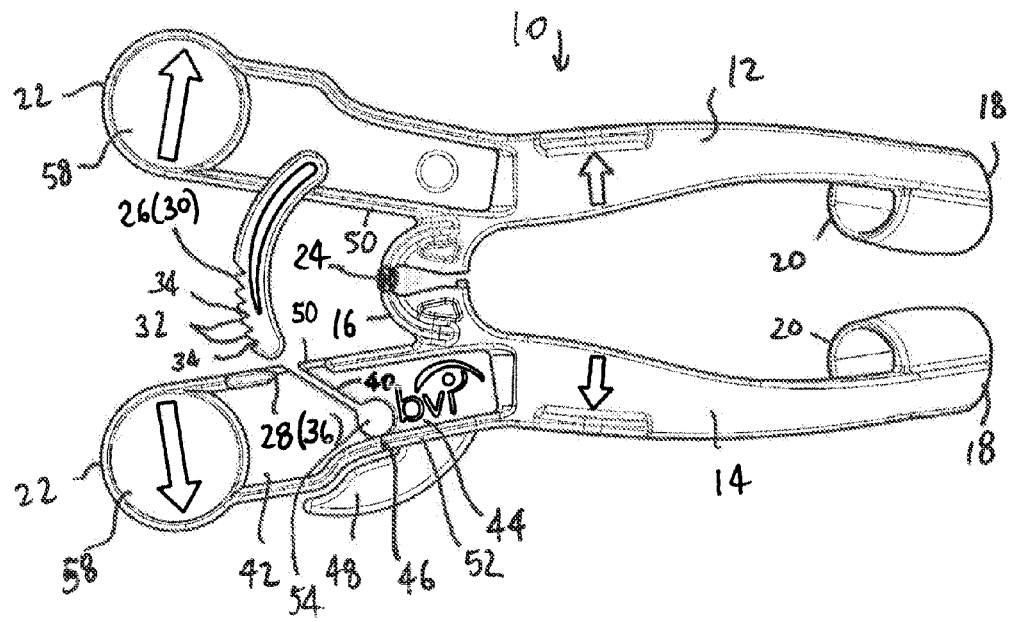
FIG. 4 is a top plan view of a speculum formed in accordance with the subject invention in a pre-use state.

With reference to FIGS. 1 and 4, in the initial pre-use state, the first and second elements 26, 28 are preferably separated and out of contact. The speculum 10 may be maintained in the pre-use state through inherent memory provided to the speculum 10 during manufacturing.

Figure 5:
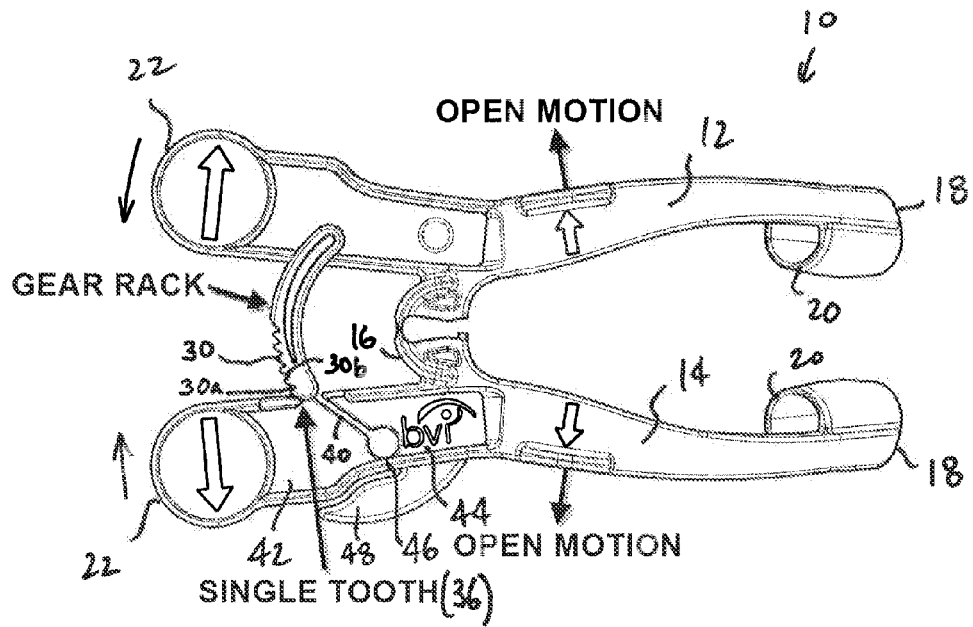

During use, and, as shown in FIG. 5, with initial coming together of the proximal ends 22 of the first and second arms 12, 14, and resulting separation of the distal ends 18 in opening the speculum 10, the first element 26 is caused to engage the second element 28, particularly with the teeth 30 by-passing the pointer 36. Preferably, the first and second arms 12, 14 may be engaged between the hinge 16 and the distal ends 18 to cause opening of the speculum 10. Alternatively, or in addition, the proximal ends 22 may be engaged to cause opening of the speculum 10. The pointer 36 imparts resistance against separation of the distal ends 18 due to interfering interengagement with the teeth 30. A threshold amount of force allows such resistance to be overcome to permit adjustment of the teeth 30 relative to the pointer 26.

With the pointer 36 nesting between adjacent pairs of the teeth 30, as shown in FIG. 6, the relative positions of the first and second arms 12, 14 may be adjusted and maintained as needed. Thus, the states shown in FIGS. 5 and 6, adjusted from the pre-use state of FIG. 4, may be achieved and maintained.

The speculum 10 is used to open the eyelids of a patient and to maintain that opened state. The degree to which the eyelids are opened may be adjusted as described above. It is noted that the eyelids may impart a reactionary closing force against the speculum 10. The threshold level of resistance against relative movement generated by the first and second elements 26, 28 must be greater than the closing force applied by the eyelids.

The force of retention to maintain the interengagement of the first and second elements 26, 28, such as in the state shown in FIG. 6, is imparted at least in part by the inherent memory of the constituent material of the speculum 10. To enhance the retentive force, a slot 40 is defined in the second arm 14 to partially separate a first portion 42 of the second arm 14 from a second portion 44 of the second arm 14 with the first portion 42 being displaceable away from the second portion 44. The second element 28, which may be in the form of the pointer 36, is located on the first portion 42 of the second arm 14. A connecting portion 46 extends between, and connects, the first and second portions 42, 44.

The first portion 42 is initially in an unstressed rest state as shown in FIGS. 1 and 4. The connecting portion 46 acts as a fulcrum for permitting rotation of the first portion 42 relative to the second portion 44 in displacement of the first portion 42 from the rest state and away from the second portion 44. In addition, with displacement of the first portion 42 from the rest state and away from the second portion 44, the connecting portion 46 acts as a "living hinge" which generates a reactive biasing force applied to the first portion 42 which urges the first portion 42 towards the rest state. This biasing force acts to provide additional retentive force to the second element 28 against the first element 26 in counteracting at least a portion of the reactionary closing force generated by the eyelids during opening of the speculum 10.

With the first and second elements 26, 28 being in interengagement, e.g., as shown in FIG. 6, it is preferred that the first portion 42 be in the rest state. Alternatively, the first portion 42 may be in a state displaced from the rest state (away from the second portion 44) with the first and second elements 26, 28 being in interengagement. This causes the connecting portion 46 to apply a biasing force to the first portion 42 which urges the first portion 42 towards the rest state. This biasing force provides additional retentive force to the second element 28 against the first element 26. In addition, displacement of the first portion 42 away from the second portion 44 allows for separation of the first and second elements 26, 28 (FIG. 8).

It is preferred that displacement of the first portion 42 relative to the second portion 44 be limited. In particular, it is preferred that the connecting portion 46 not be over stressed so as to cause yielding or plastic deformation thereof. It is desired to maintain the deformation of the connecting portion 46 within limits of elastic deformation.

To limit the range of displacement of the first portion 42 relative to the second portion 44, it is preferred that a stop member 48 be provided which extends from the second portion 44 and is configured to limit rotation of the first portion 42 about the connecting portion 46 in being displaced away from the second portion 44. The stop member 48 is configured to physically contact, and limit movement of, the first portion 42, as shown in FIGS. 8 and 9, within a predetermined range of motion based on the material characteristics of the constituent material of the speculum 10. It is preferred that the stop member 48 limit the movement of the first portion 42 inside of the elastic range of motion of the connecting portion 46 with avoidance of approaching any yielding or plastic deformation thresholds.

Figure 8:
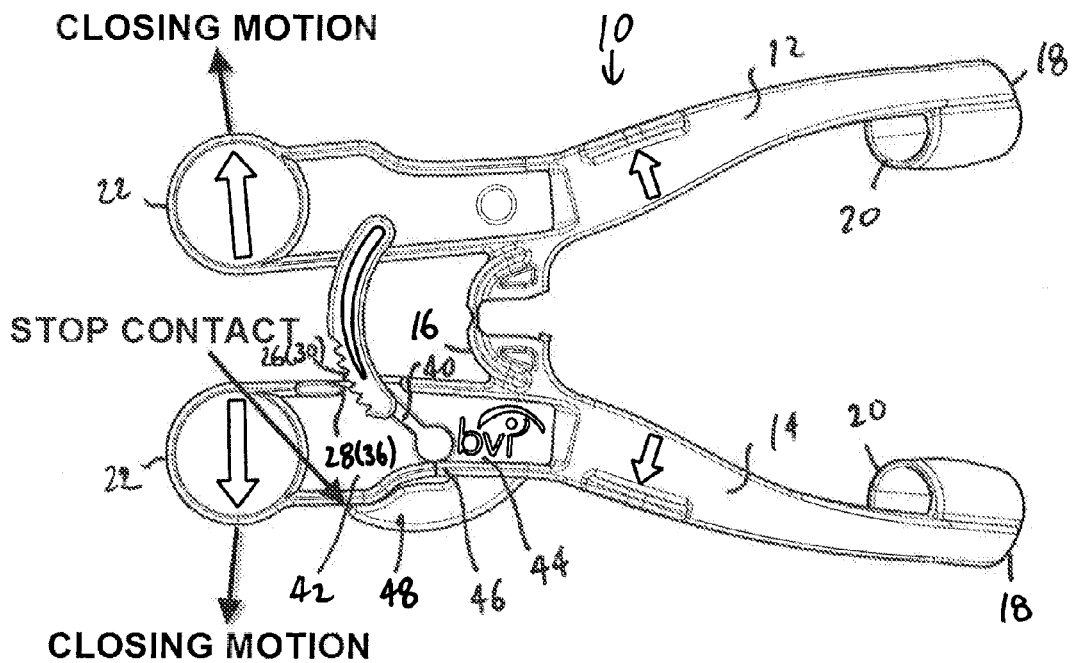
Figure 9:
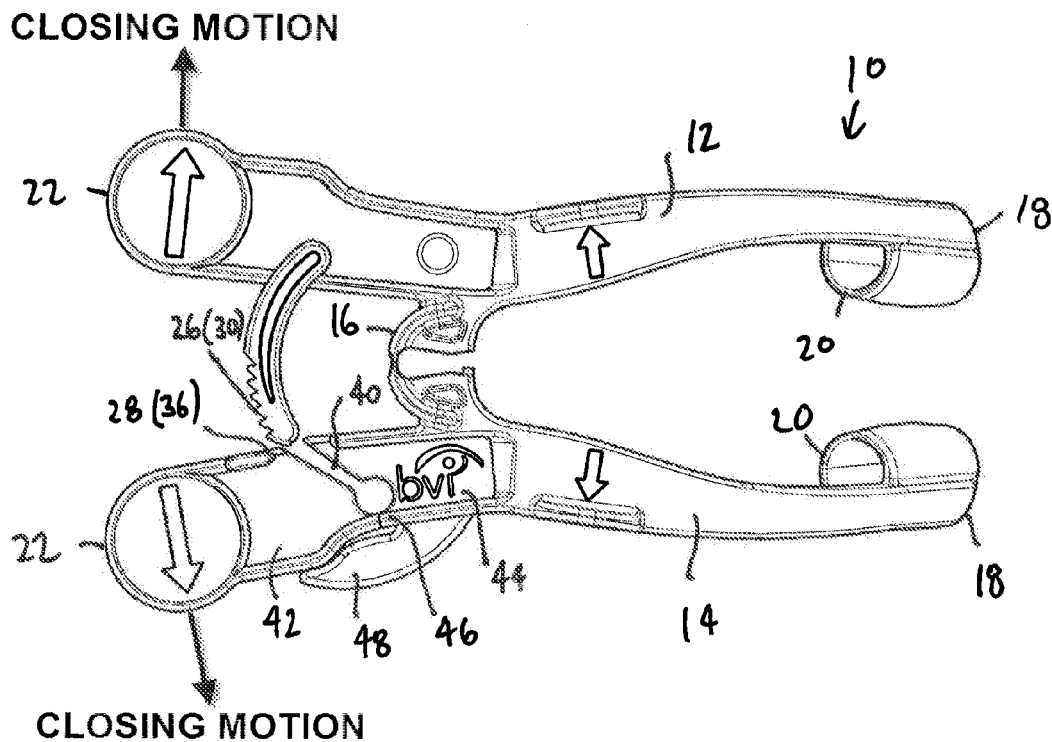

With reference to FIGS. 7-9, the speculum 10 may be closed after a procedure so as to be released from a patient's eyelids. To cause closing, the proximal ends 22 may be caused to move apart. As a result, the distal ends 18, and hence the channels 20, move closer together. The interengagement of the first and second elements 26, 28 may be forcibly overcome, whereby the pointer 36 is caused to traverse the teeth 30 in a ratcheting fashion. The connecting portion 46 may permit responsive movement of the second element 28 in and out of interengagement with the first element 26 during such adjustment. Alternatively, and more preferably, the first portion 42 is caused to be displaced away from the second portion 44 with the second element 28 coming out of interengagement with the first element, as shown in FIG. 8. This separation allows for the first and second arms 12, 14 to be rotated to the closed position with no or minimal resistance generated between the first and second elements 26, 28. As shown in FIG. 9, the first and second elements 26, 28 may be caused to be separated and spaced apart in a closed state of the speculum 10.

It is noted that the teeth 30 may be configured to be generally one-way passable having ramped surfaces 30a facing the pointer 36 and having steep surfaces 30b facing away from the pointer 36 (FIG. 5). This arrangement allows for the pointer 36 to ride over and by-pass the ramped surfaces 30a in opening the speculum 10. However, the steep surfaces 30b are configured with little or no angle relative to the pointer 36 so as to inhibit or limit reverse movement of the pointer 36 relative to the teeth 30 in the closing direction. Displacement of the first portion 42 to separate the pointer 36 from the teeth 30 may be relied upon to permit reverse adjustment of the pointer 36 relative to the teeth 30. With this arrangement, the teeth 30 and the pointer 36 may be configured to have tight interengagement which further enhances the retention generated therebetween.

Figure 10:
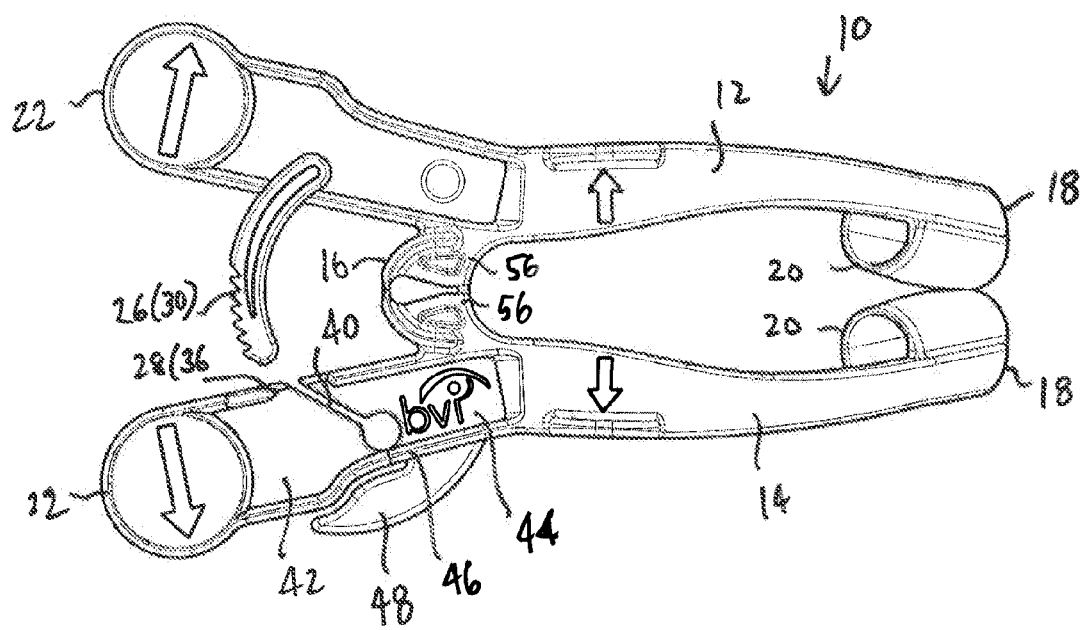

With reference to FIG. 10, inward rotation of the first and second arms 12, 14 may be limited by contact between the channels 20 or the distal ends 18. In addition, or alternatively, stop blocks 56 may be provided on the hinge 16, as shown in FIG. 10, which are configured to come into contact to limit inward motion of the first and second arms 12, 14. Conversely, outward rotation of the first and second arms 12, 14 may be limited by contact between the proximal ends 22 of the first and second arms 12, 14. In addition, or alternatively, the first element 26 may be configured to limit or inhibit outward range of movement. For example, the teeth 30 may be arranged to extend over a length coinciding with the desired range of motion. The first element 26 can be configured such that motion of the pointer 36 past the teeth 30 in the opening direction is limited or inhibited, e.g., with the first element 26 being configured to interferingly engage the pointer 36 past the teeth 30 in creating a stop or frictional engagement therewith which inhibits further movement.

Preferably, the slot 40 extends from an inner edge 50 of the second arm 14 and the stop member 48 extends from an outer edge 52 of the second arm 14 (FIG. 4). The hinge 16 extends between the inner edges 50 of the first and second arms 12, 14. It is also preferred that the slot 40 be located between the hinge 16 and the proximal end 22 of the second arm 14. The slot 40 preferably terminates with an enlarged end 54, past which the connecting portion 46 extends. The enlarged end 54 is preferably circular in shape. The enlarged end 54 acts as a stress relief to limit breaks or cracks propagating from the slot 40, particularly with displacement of the first portion 42.

The connecting portion 46 is preferably slender in a direction along a longitudinal axis of the second arm 14 to allow for bending thereabout. To provide sufficient inherent memory in the connecting portion 46 to generate the biasing force described above, as shown in FIG. 1, it is preferred that the connecting portion 46 be formed with increased thickness in a direction perpendicular to the longitudinal axis of the second arm 14 as compared to surrounding regions of the speculum 10, particularly regions of the first and second portions 42, 44 adjacent the slot 40 and the connecting portion 46.

To facilitate adjustment of the speculum 10, the proximal ends 22 may be configured to define finger tabs 58, as shown in FIGS. 1 and 4. The finger tabs 58 may be formed solid with a concave or textured surface to enhance frictional engagement therewith. Alternatively, an aperture (not shown) may be formed in the finger tabs 58 which allows for partial or whole insertion of a user's fingers.

Figure 2:
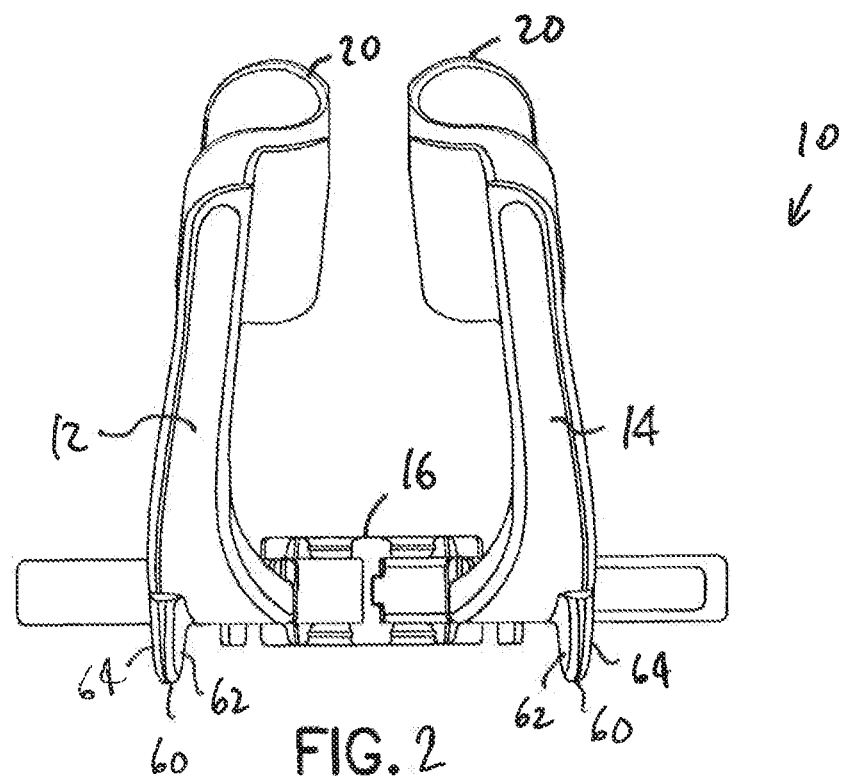
FIGS. 2 and 3 are, respectively, front and back elevational views of a speculum formed in accordance with the subject invention.

In addition, or alternatively, to facilitate adjustment of the speculum 10, one or more tabs 60 may be formed to extend from the first arm 12 and/or the second arm 14, as shown in FIGS. 1-3. The tabs 60 each include an engagement surface 62 configured to be pressingly engaged to cause the first and second arms 12, 14 to be opened. As will be appreciated by those skilled in the art, one of the tabs 60 may be provided on one of the first or second arms 12, 14 which would permit relative motion between the first and second arms 12, 14. The tabs 60 may also include secondary engagement surfaces 64, each disposed to face away from the corresponding engagement surface 62, formed to be pressingly engaged to cause the first and second arms 12, 14 to move towards a closed position. It is preferred that the tabs 60 be located between the hinge 16 and the channel 20 of the respective arm 12, 14. The tabs 60 may be provided on a speculum 10 (formed as described above) which does not include the slot 40. It is preferred that the tabs 60 be provided on each of the first and second arms 12, 14 where the slot 40 is provided.

What is claimed is:

1. A speculum comprising:
a first arm having distal and proximal ends, a first channel formed thereon at said distal end adapted to a shape of an eyelid;
a second arm having distal and proximal ends, a second channel formed thereon at said distal end adapted to a shape of an eyelid;
a hinge connected to said first and second arms, said hinge permitting said first and second arms to selectively rotate about an axis of rotation, said selective rotation causing said first and second channels to selectively move closer and farther apart;
a first element on said first arm, said first element including a plurality of teeth; and,
a second element on said second arm, said second element including a pointer formed to nest within a recess defined between adjacent ones of said plurality of teeth,
wherein said first and second elements are configured to cooperatively retain said first and second arms in select rotational positions with interfering interengagement between said first and second elements limiting said selective rotation of said first and second arms,
wherein a slot is defined in said second arm to partially separate a first portion of said second arm from a second portion of said second arm, said first portion being displaceable away from said second portion, said second element being located on said first portion, said proximal end of said second arm being located on said first portion, said interfering interengagement being defined with at least a portion of said first element extending across a portion of said slot and with said pointer being nested in said recess,
wherein said second arm includes a connecting portion extending between, and connecting, said first and second portions, said connecting portion acting as a fulcrum for permitting rotation of said first portion relative to said second portion in the displacement of said first portion relative to said second portion, the displacement of said first portion away from said second portion causing said slot to widen, and
wherein a stop member extends from said second portion configured to limit the rotation of said first portion relative to said second portion about said connecting portion in the displacement of said first portion away from said second portion, said stop member extending from an area of an outer edge of said second arm away from said first arm, said area being located on said second portion between said first portion and said distal end of said second arm.

2. The speculum as in claim 1, wherein the displacement of said first portion away from said second portion allows said second element to separate from the interfering interengagement with said first element.

3. The speculum as in claim 1, wherein a first tab extends from said first arm, said first tab defining an engagement surface configured to be pressingly engaged for causing the selective rotation wherein said first channel moves away from said second channel, said first tab being located between said hinge and said first channel.

4. The speculum as in claim 3, wherein a second tab extends from said second arm, said second tab defining an engagement surface configured to be pressingly engaged for causing the selective rotation wherein said first and second channels move apart, said second tab being located between said hinge and said second channel.

5. The speculum as in claim 1, wherein a tab extends from said second arm, said tab defining an engagement surface configured to be pressingly engaged for causing the selective rotation wherein said second channel moves away from said first channel, said tab being located between said hinge and said second channel.

* * * * *